(12) United States Patent
Imai et al.

(10) Patent No.: US 10,746,168 B2
(45) Date of Patent: Aug. 18, 2020

(54) TUBE PUMP AND HOLDING MECHANISM

(71) Applicant: Surpass Industry Co., Ltd., Saitama (JP)

(72) Inventors: Hiroshi Imai, Saitama (JP); Kazuki Hirai, Saitama (JP); Yukinobu Imai, Saitama (JP)

(73) Assignee: Surpass Industry Co., Ltd., Saitama (JP)

( * ) Notice: Subject to any disclaimer, the term of this patent is extended or adjusted under 35 U.S.C. 154(b) by 248 days.

(21) Appl. No.: 15/891,878

(22) Filed: Feb. 8, 2018

(65) Prior Publication Data

US 2018/0230987 A1 Aug. 16, 2018

(30) Foreign Application Priority Data

Feb. 14, 2017 (JP) ................. 2017-025167

(51) Int. Cl.
| F04B 43/08 | (2006.01) |
| F04B 43/00 | (2006.01) |
| F04B 43/12 | (2006.01) |
| F04B 53/22 | (2006.01) |
| A61M 1/10 | (2006.01) |

(52) U.S. Cl.
CPC ......... *F04B 43/082* (2013.01); *A61M 1/1039* (2014.02); *F04B 43/0072* (2013.01); *F04B 43/086* (2013.01); *F04B 43/1238* (2013.01); *F04B 43/1253* (2013.01); *F04B 53/22* (2013.01)

(58) Field of Classification Search
None
See application file for complete search history.

(56) References Cited

U.S. PATENT DOCUMENTS 3,737,257 A * 6/1973 DeVries ............... F04B 43/1253
                                                        417/477.8
4,518,327 A * 5/1985 Hackman ............ F04B 43/1253
                                                        417/477.3
(Continued)

FOREIGN PATENT DOCUMENTS

DE     2452771 A1   5/1976
EP     3061473 A1   8/2016
(Continued)

OTHER PUBLICATIONS

Partial European Search report dated Aug. 8, 2018 in corresponding application EP18155218.3.

(Continued)

*Primary Examiner* — Peter J Bertheaud
*Assistant Examiner* — Geoffrey S Lee
(74) *Attorney, Agent, or Firm* — Muncy, Geissler, Olds & Lowe, P.C.

(57) ABSTRACT

To provide a tube pump which includes: a drive mechanism including a first roller unit and a second roller unit which rotate about an axis line while being in contact with a tube having elasticity, and a first drive unit and a second drive unit which cause the first roller unit and the second roller unit to rotate independently about the axis line; a holding mechanism which holds the tube in an arcuate shape about the axis line; and an attachment mechanism which detachably attaches the holding mechanism to the drive mechanism.

5 Claims, 12 Drawing Sheets

(56) References Cited

U.S. PATENT DOCUMENTS

| | | | | |
|---|---|---|---|---|
| 4,558,996 | A * | 12/1985 | Becker | F04B 43/1253 417/374 |
| 5,062,775 | A * | 11/1991 | Orth | A61M 1/10 417/319 |
| 5,681,257 | A * | 10/1997 | Letourneur | B04B 9/08 403/325 |
| 6,095,772 | A * | 8/2000 | Ramey | F04D 29/20 417/319 |
| 7,547,200 | B2 * | 6/2009 | O'Mahony | F04B 43/1253 417/477.12 |
| 8,840,382 | B2 * | 9/2014 | Al-Harbi | A61M 1/1037 417/477.11 |
| 9,033,940 | B2 * | 5/2015 | Muri | A61M 1/0058 604/294 |
| 9,103,340 | B2 | 8/2015 | Wagner | |
| 9,388,803 | B2 * | 7/2016 | Schaefer | F04B 43/08 |
| 9,562,529 | B2 * | 2/2017 | Schaefer | F04B 45/06 |
| 9,999,712 | B2 * | 6/2018 | Zhu | A61M 1/1039 |
| 2002/0151838 | A1 | 10/2002 | Beck et al. | |
| 2007/0140880 | A1 * | 6/2007 | Fulmer | F04B 43/1253 417/477.1 |
| 2010/0129247 | A1 * | 5/2010 | Lauer | F04B 43/1276 417/477.8 |
| 2010/0166578 | A1 * | 7/2010 | Watson | F04D 13/10 417/423.3 |
| 2012/0248149 | A1 * | 10/2012 | Pelfrey | B67D 1/108 222/214 |
| 2014/0012201 | A1 * | 1/2014 | Schaefer | F04B 43/12 604/151 |
| 2016/0245271 | A1 * | 8/2016 | Schaefer | A61M 1/1603 |
| 2017/0028117 | A1 * | 2/2017 | Mochizuki | A61M 5/14232 |
| 2018/0230987 | A1 * | 8/2018 | Imai | F04B 43/086 |

FOREIGN PATENT DOCUMENTS

| | | |
|---|---|---|
| JP | H05-263765 A | 10/1993 |
| WO | WO2011057663 A1 | 5/2011 |

OTHER PUBLICATIONS

Extended European Search report dated Nov. 21, 2018 in corresponding application EP18155218.3.

* cited by examiner

TUBE PUMP AND HOLDING MECHANISM

CROSS-REFERENCE TO RELATED APPLICATIONS

This application is based on Japanese Patent Application No. 2017-025167, the contents of which are incorporated herein by reference in its entirety.

TECHNICAL FIELD

The present disclosure relates to a tube pump and a holding mechanism.

BACKGROUND ART

Conventionally, there has been known a pump where a pair of pressing elements are rotated so as to press a tube thus displacing a liquid from one end side to the other end side of the tube (for example, see Japanese Unexamined Patent Application, Publication No. Hei5-263765 (hereinafter referred to as PTL 1)).

In the pump disclosed in PTL 1, a rotary shaft to which one pressing element is connected is projected upward, and a rotary shaft to which the other pressing element is connected is projected downward. The pump disclosed in PTL 1 is configured such that drive forces of a pair of electric motors are respectively transmitted to the rotary shafts, which project upward and downward, through a pair of reducers so that the pair of pressing elements are rotated at non-constant velocities thus displacing the liquid by small pulsation.

The pump disclosed in PTL 1 includes a drum having an arcuate inner peripheral surface and a tube disposed on the inner peripheral surface of the drum. The pump is configured such that the rotary shafts connected to the pair of pressing elements and a drive mechanism for driving the rotary shafts project upward and downward from the drum.

SUMMARY

Technical Problem

In replacing a liquid to be conveyed by the pump, it is common to clean a tube with pure water or the like and reuse the tube or to replace the tube per se. Particularly, in a field of bioscience such as regenerative medicine, it is more common to replace the tube per se.

In the pump disclosed in PTL 1, however, the drive mechanism and the like are disposed above and below the drum where the tube is disposed on the inner peripheral surface of the drum. Accordingly, the tube disposed on the inner peripheral surface of the drum cannot be easily replaced.

The present disclosure has been made under such circumstances, and it is an object of the present disclosure to provide a tube pump where each of a pair of contact members, which rotate while being in contact with a tube, can be rotated independently, and the tube can be easily replaced.

Solution to Problem

To solve the above-described problem, the present disclosure employs the following solutions.

According to one aspect of the present disclosure, there is provided a tube pump which includes: a drive mechanism including a pair of contact members configured to rotate about an axis line while being in contact with a tube having elasticity, and a pair of drive units configured to cause the pair of contact members to rotate independently about the axis line; a holding mechanism configured to hold the tube in an arcuate shape about the axis line; and an attachment mechanism configured to detachably attach the holding mechanism to the drive mechanism.

According to the tube pump of one aspect of the present disclosure, the drive mechanism includes the pair of contact members and the pair of drive units. Accordingly, the pair of contact members, which rotate while being in contact with the tube held by the holding mechanism in an arcuate shape about the axis line, can be independently rotated about the axis line.

According to the tube pump of one aspect of the present disclosure, the holding mechanism is detachably attached to the drive mechanism by the attachment mechanism so that the tube can be easily replaced.

The tube pump according to one aspect of the present disclosure may be configured such that the tube pump further includes a control unit configured to control the pair of drive units, wherein the control unit is capable of performing a first control mode where the pair of contact members are rotated in the same direction so as to convey a liquid in the tube, and a second control mode where positions of the pair of contact members disposed about the axis line are respectively fixed so as to prevent the pair of contact members from coming into contact with the tube.

According to the tube pump having such a configuration, by performing the second control mode, the pair of contact members can be fixed so as to prevent a contact with the tube. Accordingly, in attaching the holding mechanism to the drive mechanism by the attachment mechanism, the holding mechanism can be easily and reliably attached to the drive mechanism while preventing the tube from coming into contact with the pair of contact members. Further, by performing the first control mode after the holding mechanism is attached to the drive mechanism by the attachment mechanism, a liquid in the tube can be conveyed.

In the tube pump having the above-mentioned configuration, the attachment mechanism may include: a housing mechanism configured to house the holding mechanism; and an advancing and retracting mechanism configured to advance and retract the housing mechanism along the axis line, and the advancing and retracting mechanism may be a mechanism capable of changing over a state of the tube pump between a mounting state where the tube and the pair of contact members are disposed at the same position on the axis line and a separated state where the holding mechanism is disposed at a position separated from the drive mechanism by a distance.

According to the tube pump of this aspect, the holding mechanism which is housed in the housing mechanism is made to advance and retract along the axis line by the advancing and retracting mechanism. With such a configuration, a state of the tube pump can be changed over reliably between the separated state and the mounting state while preventing the tube from coming into contact with the contact member and the like.

In the tube pump of the above-mentioned aspect, the control unit may be configured to control the advancing and retracting mechanism so as to change over a state of the tube pump between the mounting state and the separated state, and the control unit may be configured to perform the second control mode in changing over the state of the tube pump from the separated state to the mounting state.

With such a configuration, in attaching the holding mechanism to the drive mechanism, the second control mode is performed by the control unit so that the pair of contact members are fixed at the position where the pair of contact members do not come into contact with the tube. Thereafter, the state of the tube pump is changed over from the separated state to the mounting state. Accordingly, in attaching the holding mechanism to the drive mechanism, an operator is required to perform only a relatively simple operation, that is, to house the holding mechanism in the housing mechanism.

According to another aspect of the present disclosure, there is provided a holding mechanism configured to be detachably attached to a drive mechanism including a pair of contact members which rotate about an axis line while being in contact with a tube having elasticity, the holding mechanism including: a holding portion on which an inner peripheral surface is formed, the holding portion holding the tube in an arcuate shape about the axis line; and a pair of fixing portions configured to house and fix a pair of positioning members attached to an outer peripheral surface of the tube, wherein the inner peripheral surface is formed in a range larger than 180 degrees about the axis line.

According to the holding mechanism of one aspect of the present disclosure, the inner peripheral surface of the holding mechanism is formed in a range large than 180 degrees about the axis line. Accordingly, when the tube is disposed along the inner peripheral surface of the holding portion, the tube comes into contact with the arcuate inner peripheral surface of the holding portion with a distance longer than a half of a circumference of an arcuate shape of the inner peripheral surface. With such a configuration, when the contact members rotate about the axis line, a range where the contact members come into contact with the tube increases. Therefore, along with the increase in such a range, an amount of a liquid which is sandwiched between the pair of contact members increases. The larger an amount of the liquid becomes, the more an increase amount of pressure of a liquid which can be increased by the tube pump increases so that pulsing of a liquid can be properly controlled.

In the holding mechanism according to one aspect of the present disclosure, the holding portion may be formed into a cylindrical shape, and one end of the holding portion in a direction of the axis line may be closed and the other end of the holding portion in the direction of the axis line may be opened.

One end of the holding portion is closed so that a problem such as damage of the tube carelessly caused by an operator can be suppressed. At the same time, the other end of the holding portion is opened so that the holding mechanism can be attached to the drive mechanism.

According to the present disclosure, it is possible to provide a tube pump where each of a pair of contact members, which rotate while being in contact with a tube, can be rotated independently, and the tube can be easily replaced.

DESCRIPTION OF EMBODIMENTS

Hereinafter, a tube pump 500 according to one embodiment of the present disclosure is described with reference to drawings.

Figure 1:
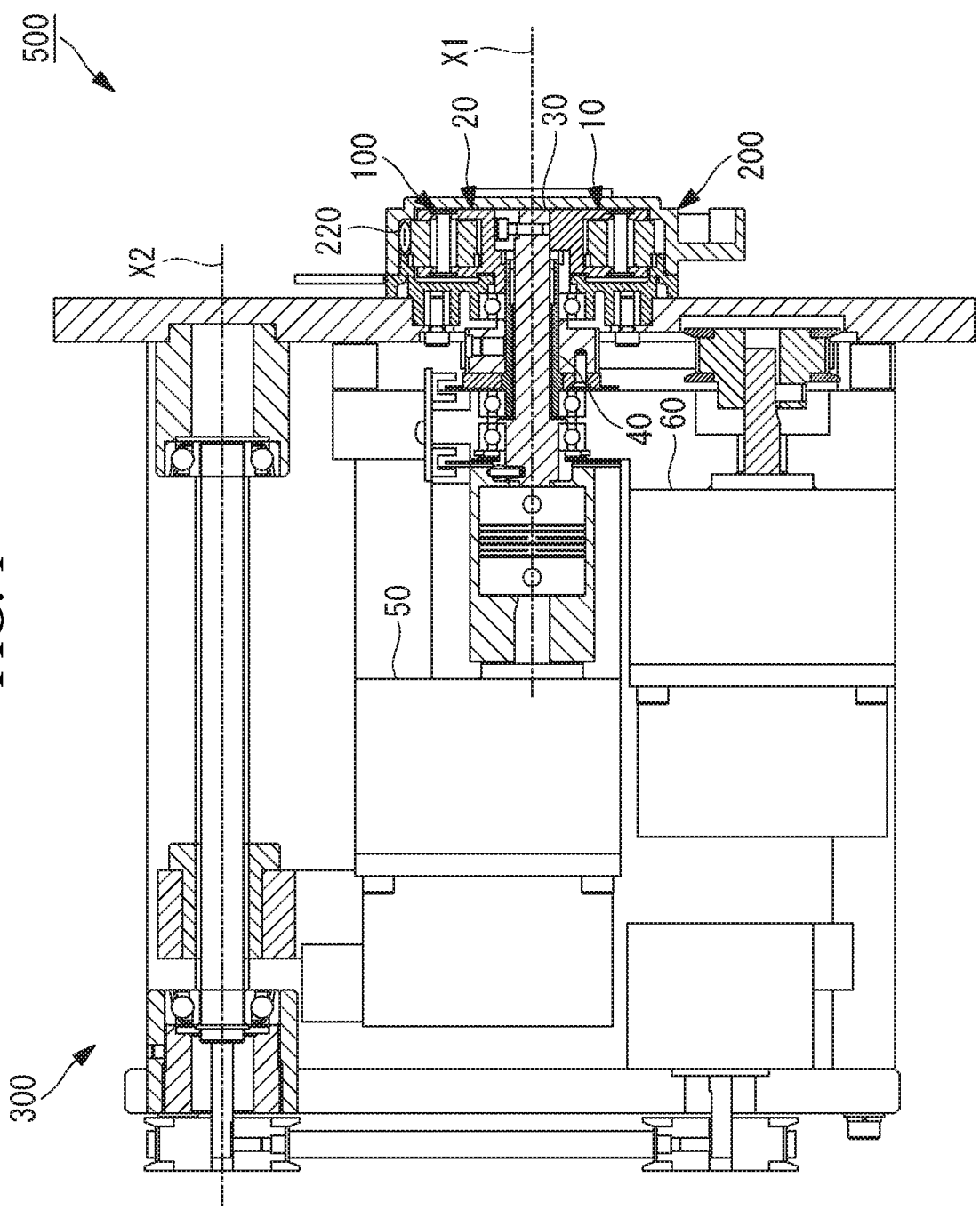
FIG. 1 is a longitudinal cross-sectional view showing one embodiment of a tube pump.
Figure 2:
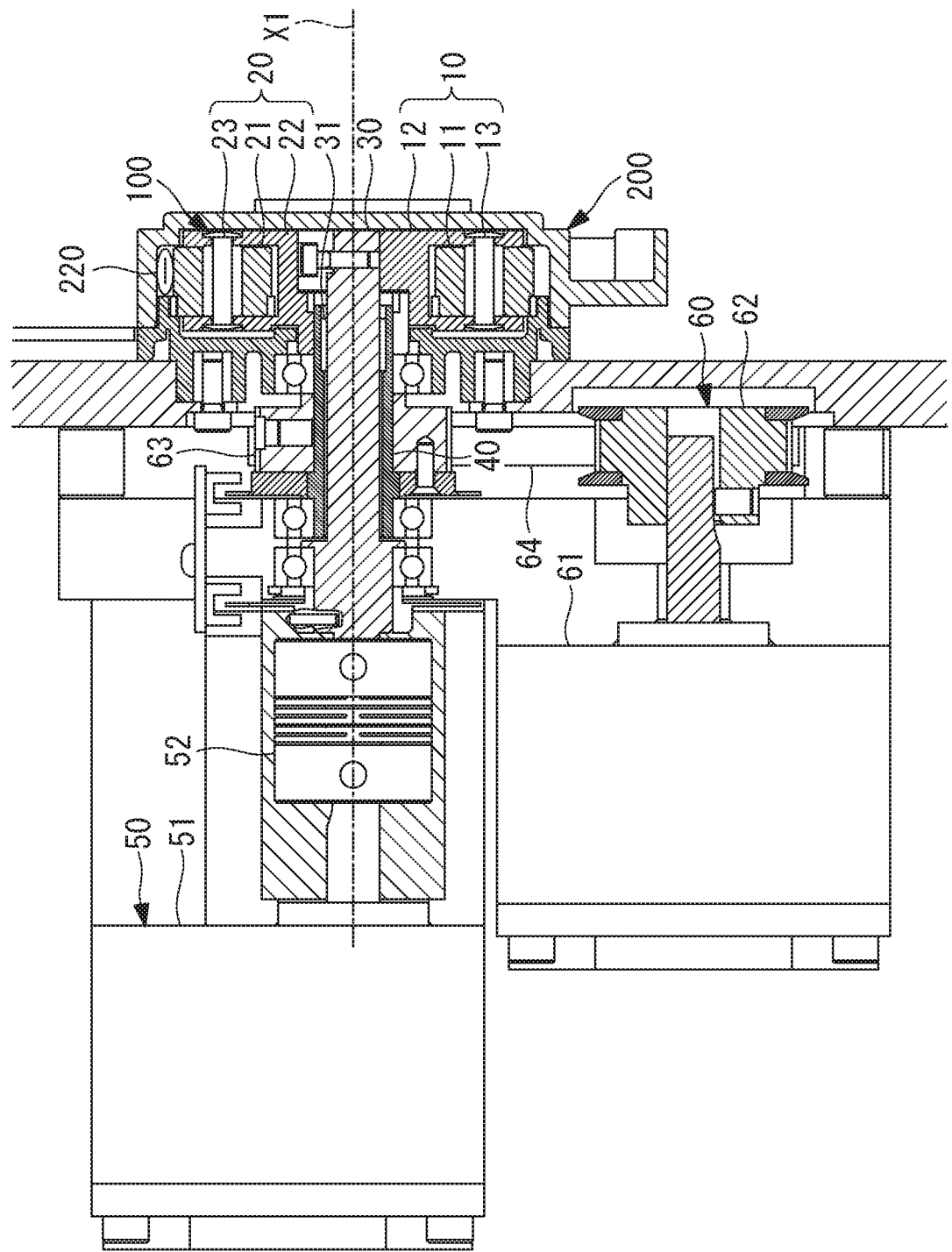
FIG. 2 is a partially enlarged view of the tube pump shown in FIG. 1.
Figure 3:
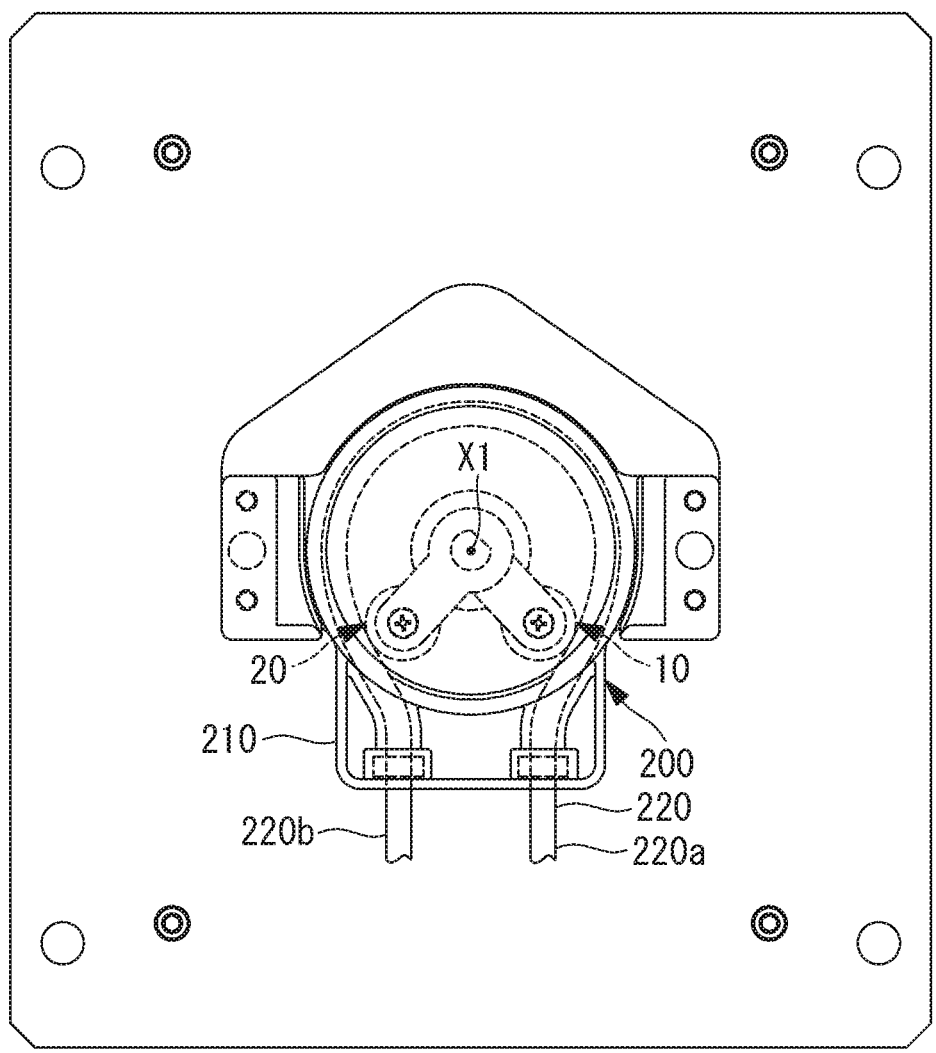
FIG. 3 is a right side view of the tube pump shown in FIG. 1.

As shown in FIG. 1 to FIG. 3, the tube pump 500 of this embodiment is an apparatus where a first roller unit 10 (first contact member) and a second roller unit 20 (second contact member) are rotated in the same direction about an axis line X1 so that a fluid which flows into a tube 220 from an inflow side 220a and is in the tube 220 is displaced to an outflow side 220b.

As shown in FIG. 1, the tube pump 500 of this embodiment includes: a drive mechanism 100 for driving the first roller unit 10 and the second roller unit 20; a holding mechanism 200 for holding the tube 220; an attachment mechanism 300 for detachably attaching the holding mechanism 200 to the drive mechanism 100; and a control unit 400 not shown in the drawing. Hereinafter, respective parts included in the tube pump 500 are described.

First, the drive mechanism 100 in this embodiment is described.

As shown in FIG. 1 to FIG. 3, the drive mechanism 100 in this embodiment includes: the first roller unit 10 and the second roller unit 20 which rotate about an axis line X1 while being in contact with the tube 220; a drive shaft 30 which is disposed on the axis line X1, and is connected to the first roller unit 10; a drive cylinder 40 which is connected to the second roller unit 20; a first drive unit 50 which transmits a drive force to the drive shaft 30; and a second drive unit 60 which transmits a drive force to the drive cylinder 40.

As shown in FIG. 2, the first roller unit 10 includes: a first roller 11 which rotates about an axis line extending parallel to the axis line X1 while the first roller 11 is in contact with the tube 220; a first roller support member 12 which is connected to the drive shaft 30 so as to integrally rotate with the drive shaft 30 about the axis line X1; and a first roller shaft 13 which has both end portions thereof supported by the first roller support member 12, and to which the first roller 11 is rotatably attached.

The second roller unit 20 includes: a second roller 21 which rotates about an axis line extending parallel to the axis line X1 while the second roller 21 is in contact with the tube 220; a second roller support member 22 which is connected to the drive cylinder 40 so as to integrally rotate with the drive cylinder 40 about the axis line X1; and a second roller shaft 23 which has both end portions thereof supported by the second roller support member 22, and to which the second roller 21 is rotatably attached.

The first drive unit 50 includes a first electric motor 51 and a power transmission mechanism 52. The first drive unit 50 transmits a rotational force of the first electric motor 51 to the drive shaft 30 through the power transmission mechanism 52. The first roller unit 10 rotates about the axis line X1 along with the rotation of the drive shaft 30.

The second drive unit 60 includes: a second electric motor 61; a drive pulley 62; a driven pulley 63; and a belt 64. The second drive unit 60 transmits a rotational force of the second electric motor 61 to the drive pulley 62 so as to cause the belt 64 to rotate about the axis line X1. A rotational force of the belt 64 is transmitted to an outer peripheral surface of the driven pulley 63. At this stage of operation, an inner peripheral surface of the driven pulley 63 is fixed to an outer peripheral surface of the drive cylinder 40. Accordingly, the rotational force of the belt 64 is transmitted from the driven pulley 63 to the drive cylinder 40.

As shown in FIG. 2, the drive cylinder 40 is disposed on the outer peripheral side of the drive shaft 30 with a bearing member 31 interposed between the drive cylinder 40 and the drive shaft 30. Accordingly, the drive cylinder 40 can rotate about the axis line X1 independently from the drive shaft 30. The drive shaft 30 rotates about the axis line X1 by a drive force caused by the first drive unit 50. The drive cylinder 40 rotates about the axis line X1 by a drive force caused by the second drive unit 60 independently from the drive shaft 30.

The second roller support member 22 of the second roller unit 20 is connected to the distal end side of the drive cylinder 40 so as to rotate integrally with the drive cylinder 40 about the axis line X1. Accordingly, the second roller unit 20 rotates about the axis line X1 along with the rotation of the drive cylinder 40.

Next, the displacement of a liquid performed by the tube pump 500 of this embodiment is described.

Figure 4:
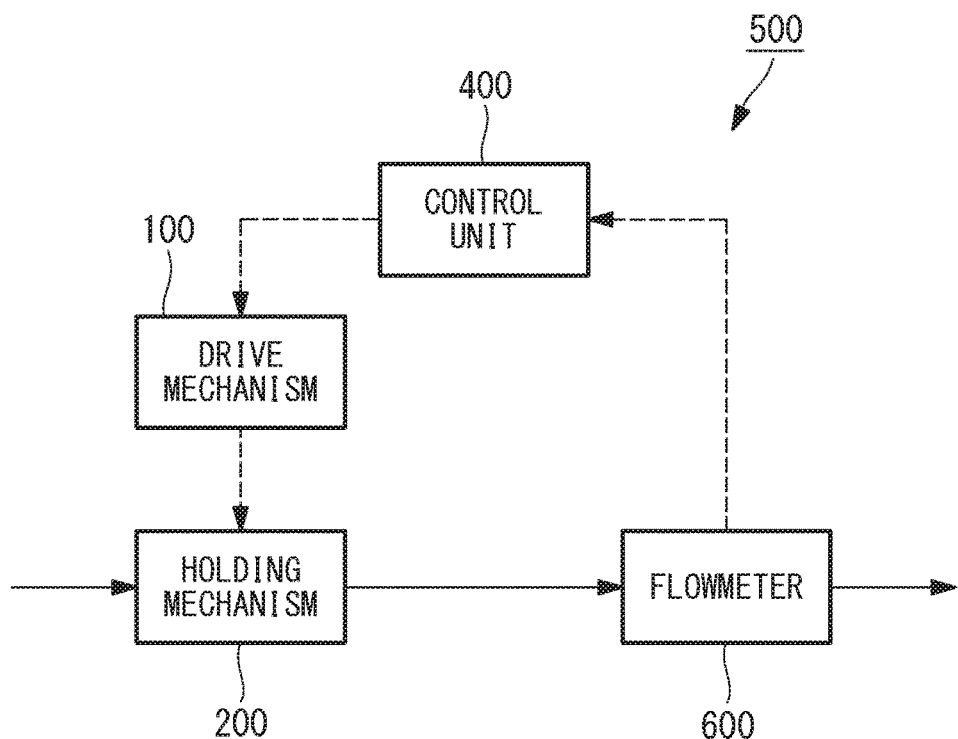
FIG. 4 is a view showing a control configuration of the tube pump according to one embodiment.

FIG. 4 is a view showing a control configuration of the tube pump 500 of this embodiment. In the tube pump 500 of this embodiment, a flow rate of a fluid displaced from the tube 220 held by the holding mechanism 200 is measured by a flowmeter 600, and the control unit 400 receives the measured result. The control unit 400 controls the drive mechanism 100 based on the received measured result such that a flow rate of a liquid measured by the flowmeter 600 assumes a desired flow rate. At this stage of the operation, the flowmeter 600 may be incorporated into the tube pump 500 as a part of the tube pump 500. Alternatively, the flowmeter 600 may be a device separated from the tube pump 500.

In the tube pump 500 shown in FIG. 4, a control signal for controlling the first drive unit 50 and the second drive unit 60 of the drive mechanism 100 is transmitted from the control unit 400 to the drive mechanism 100.

The drive mechanism 100 may be formed as a mechanism into which the control unit 400 is incorporated. In this case, the control unit 400 incorporated into the drive mechanism 100 generates a control signal for controlling the first drive unit 50 and the second drive unit 60, and transmits the control signal to the first drive unit 50 and the second drive unit 60.

Next, the holding mechanism 200 of this embodiment is described.

Figure 5:
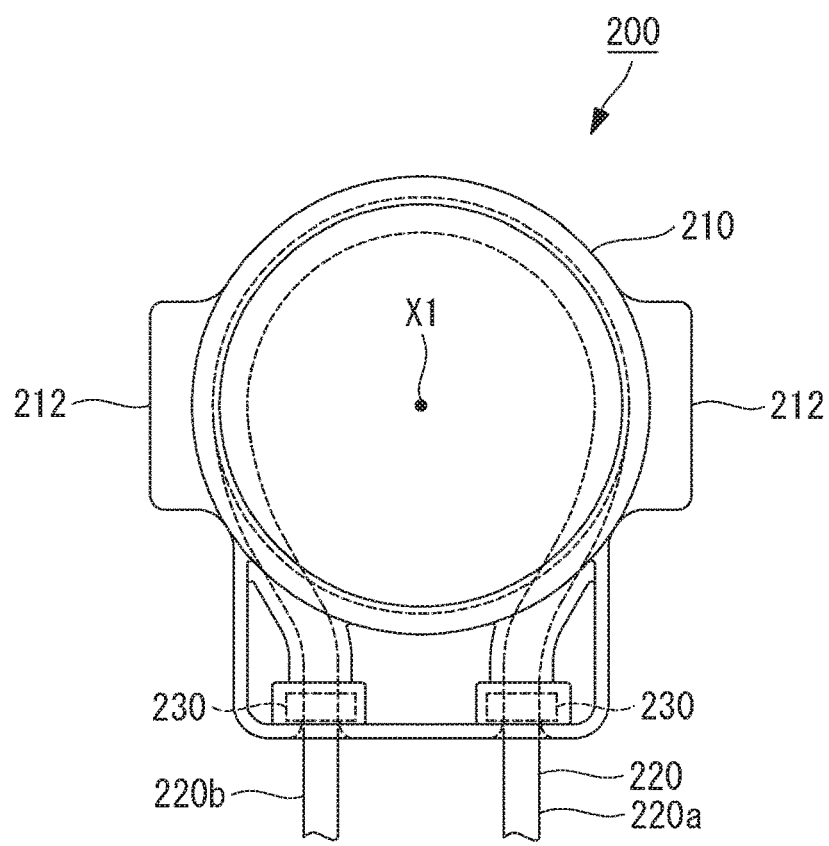
FIG. 5 is a front view of a holding mechanism.
Figure 6:
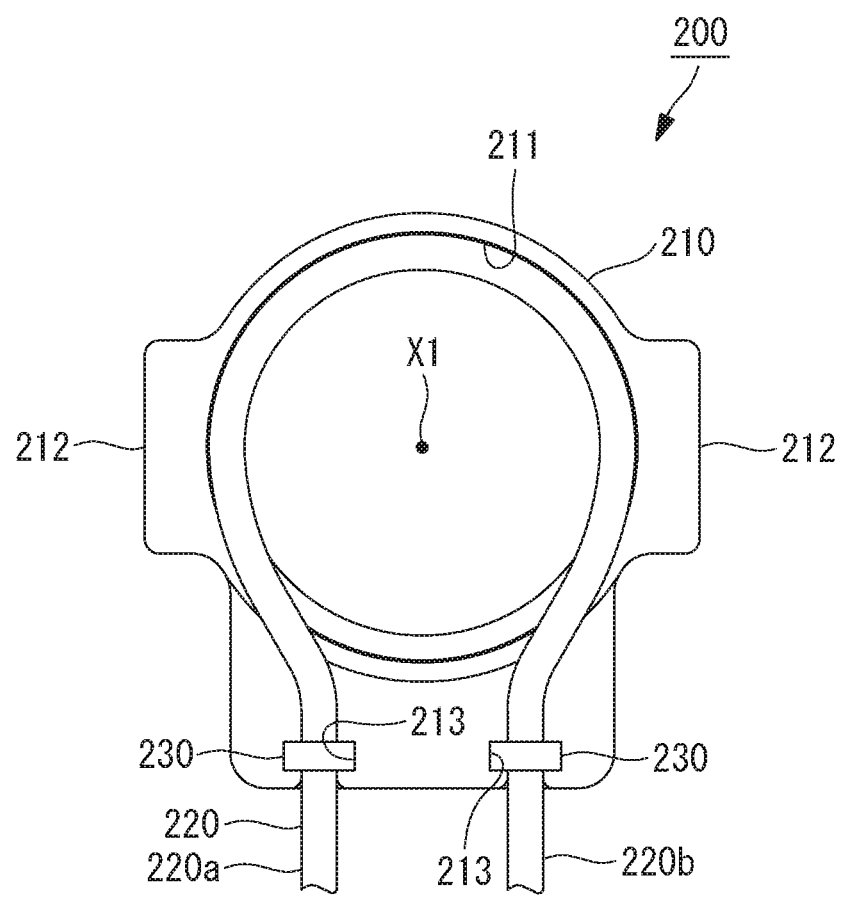
FIG. 6 is a back view of the holding mechanism.

As shown in FIG. 5 which is a front view and FIG. 6 which is a back view, the holding mechanism 200 includes: a tube case (holding portion) 210; the tube 220; and a pair of tube pressing rings 230 (positioning members).

The tube case 210 has: an inner peripheral surface 211 which holds the tube 220 in an arcuate shape about the axis line X1; a pair of projections 212 which are housed in a housing mechanism 310 of the attachment mechanism 300 described later; and a pair of fixing holes 213 for housing and fixing the pair of tube pressing rings 230. The tube case 210 is formed into a substantially cylindrical shape about the axis line X1. At the same time, the tube case 210 has a shape where one end of the tube case 210 on the front side in the direction of the axis line X1 is closed, and the other end of the tube case 210 on the back side in the direction of the axis line X1 is opened. The tube case 210 is made of a transparent or translucent resin material (for example, polycarbonate).

The tube 220 is made of a resin material (for example, silicone rubber) having elasticity. The tube 220 is a tubular member for conveying a liquid supplied from one end of the tube 220, which is a supply source, to the other end of the tube 220, which is a supply destination. The pair of tube pressing rings 230 are attached at two predetermined positions on the tube 220.

Figure 7:
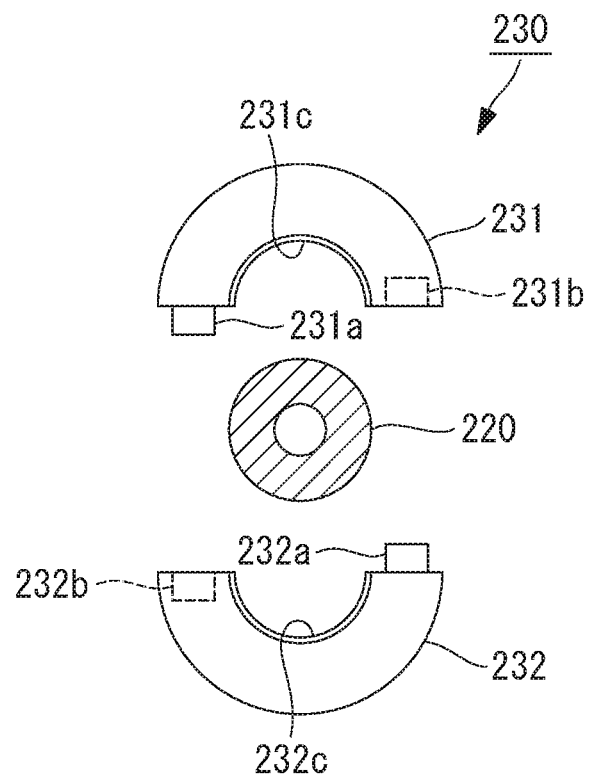
FIG. 7 is an exploded view of a tube pressing ring.

As shown in FIG. 7, each tube pressing ring 230 includes a first pressing member 231 and a second pressing member 232. A projection portion 231a, an insertion hole 231b, and a fixing groove 231c are formed on the first pressing member 231. A projection portion 232a, an insertion hole 232b, and a fixing groove 232c are formed on the second pressing member 232. The projection portion 231a is inserted into the insertion hole 232b, and the projection portion 232a is inserted into the insertion hole 231b so that the first pressing member 231 and the second pressing member 232 are connected with each other with the tube 220 interposed therebetween.

Figure 8:
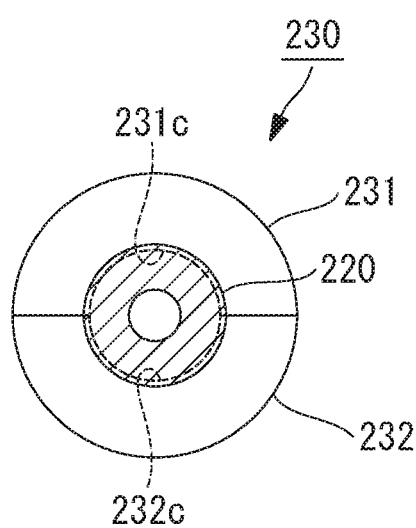
FIG. 8 is a view showing a state where the tube pressing ring is attached to a tube.

As shown in FIG. 8, in a state where the first pressing member 231 and the second pressing member 232 are connected with each other, the fixing groove 231c and the fixing groove 232c form an inner peripheral surface of the tube pressing ring 230. An inner diameter of the inner peripheral surface of the tube pressing ring 230 is smaller than an outer diameter of the tube 220 so that an outer peripheral surface of the tube 220 is elastically deformed by the fixing groove 231c and the fixing groove 232c. Accordingly, even when an external force caused by the drive mechanism 100 acts on the tube 220, a state is maintained where the tube 220 is fixed by the tube pressing rings 230.

As shown in FIG. 6, the pair of tube pressing rings 230 attached to the tube 220 are housed in and fixed to the pair of fixing holes 213 formed on the tube case 210. Positions where the pair of tube pressing rings 230 are attached to the tube 220 are adjusted such that, in a state where the pair of tube pressing rings 230 are fixed to the pair of fixing holes 213, the tube 220 is brought into contact with a whole region of the inner peripheral surface 211 of the tube case 210.

Figure 9:
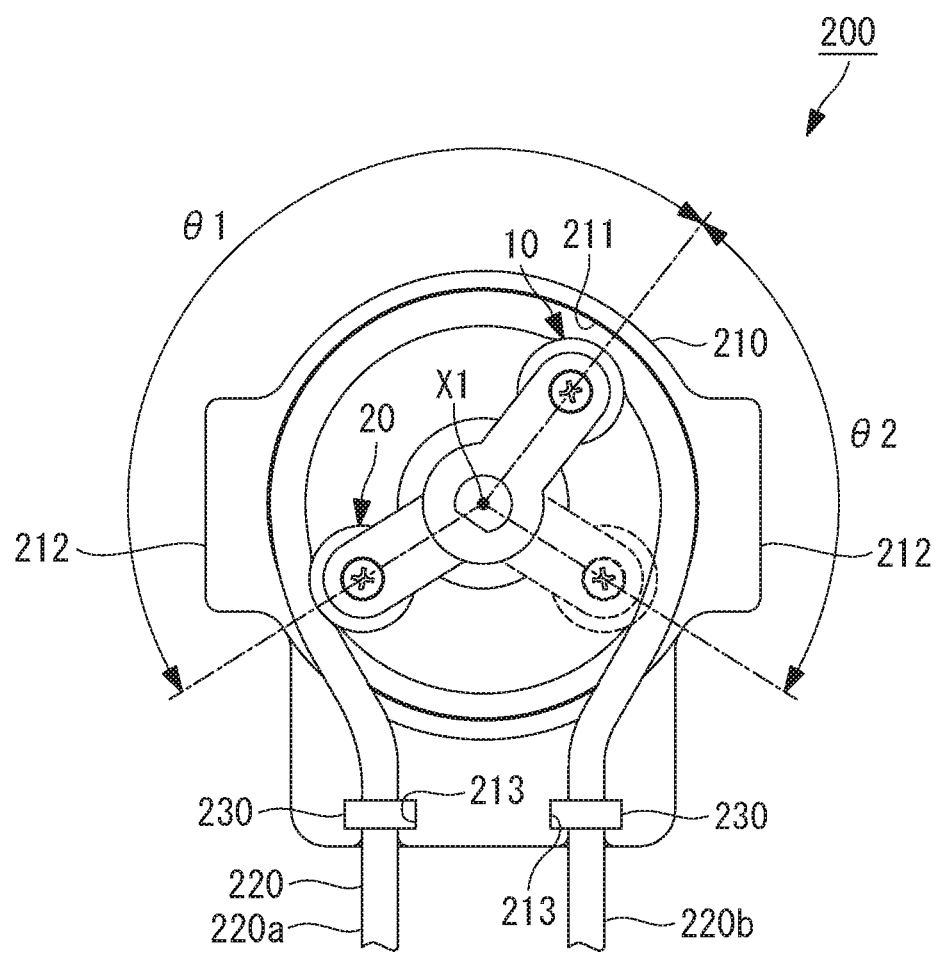
FIG. 9 is a view of the holding mechanism attached to a drive mechanism as viewed from the back side.
Figure 10:
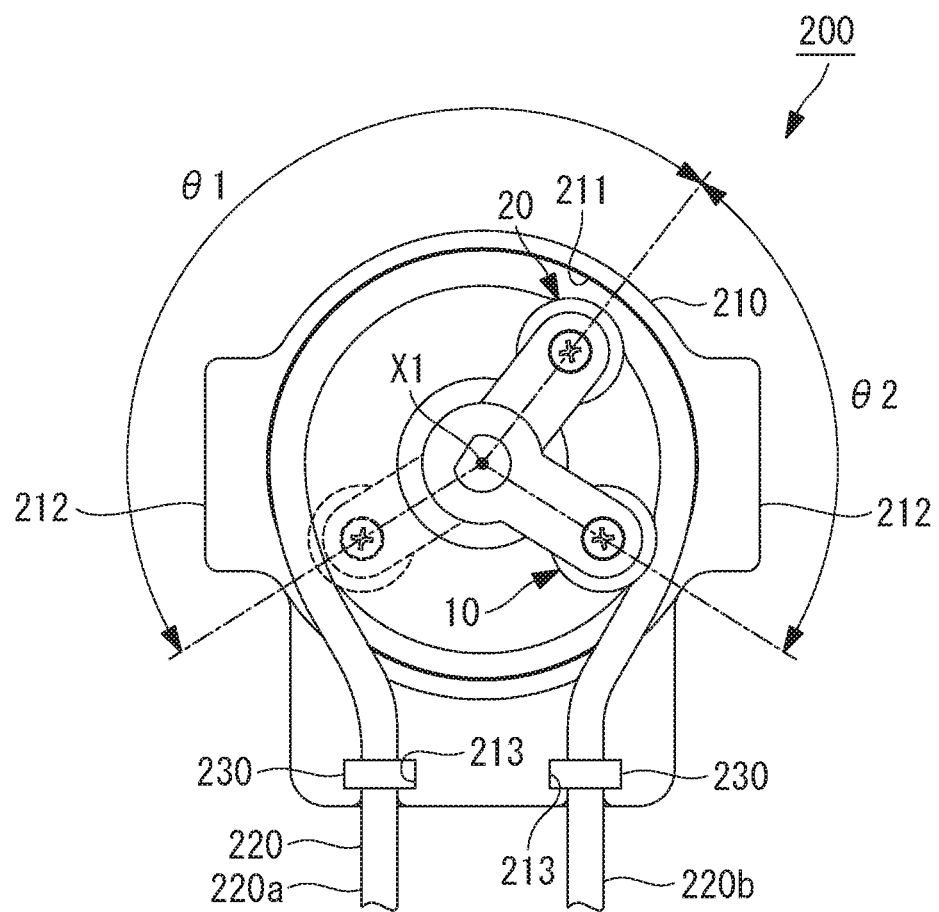
FIG. 10 is a view of the holding mechanism attached to the drive mechanism as viewed from the back side.

A range where the inner peripheral surface 211 of the tube case 210 is formed is described with reference to FIG. 9 and FIG. 10. FIG. 9 and FIG. 10 are views of the holding mechanism 200 attached to the drive mechanism 100 as viewed from the back side (drive mechanism 100 side).

The first roller unit 10 and the second roller unit 20 of the drive mechanism 100 are respectively rotated by the first drive unit 50 and the second drive unit 60 independently about the axis line X1. In FIG. 9 and FIG. 10, the first roller unit 10 and the second roller unit 20 respectively rotate in the clockwise direction about the axis line X1. When the first roller unit 10 and the second roller unit 20 are disposed so as to opposedly face the inner peripheral surface 211 of the tube case 210, the tube 220 is elastically deformed thus being compressed at the position where the respective roller units are disposed.

FIG. 9 shows a state where the first roller unit 10 moves while compressing the tube 220, and the second roller unit 20 starts to come into contact with the tube 220. When a state shown in FIG. 9 is brought about, a liquid in the tube 220 is closed within a range of an angle θ1 about the axis line X1. When the first roller unit 10 and the second roller unit 20 further rotate respectively in the clockwise direction from the state shown in FIG. 9, a state shown in FIG. 10 is brought about.

FIG. 10 shows a state where the second roller unit 20 moves while compressing the tube 220, and the first roller unit 10 starts to separate from the tube 220. When the state shown in FIG. 10 is brought about, the liquid in the tube 220 is closed within a range of an angle θ2 about the axis line X1. When the state shown in FIG. 9 and the state shown in FIG. 10 are compared with each other, the angle θ2 is narrower than the angle θ1. Accordingly, when the state of the roller units changes from the state shown in FIG. 9 to the state shown in FIG. 10, a pressure of the liquid in the tube 220 closed by the first roller unit 10 and the second roller unit 20 increases.

As described above, in the tube pump 500 of this embodiment, the first roller unit 10 and the second roller unit 20 can be rotated independently. Accordingly, by setting the angle θ2 smaller than the angle θ1 as shown in FIG. 9 and FIG. 10, it is possible to increase a pressure of a liquid to be displaced from the outflow side 220b of the tube 220. Further, when the angle θ1 and the angle θ2 are set equal to each other, it is possible to set a pressure of a liquid flowing into the tube 220 from the inflow side 220a equal to a pressure of the fluid flowing out from the tube 220 from the outflow side 220b. Further, when the angle θ2 is set larger than the angle θ1, it is possible to reduce a pressure of a liquid to be displaced from the outflow side 220b of the tube 220.

As described above, in the tube pump 500 of this embodiment, by properly adjusting the angle θ1 and the angle θ2 each of which is formed by the first roller unit 10 and the second roller unit 20, a pressure of a liquid to be displaced from the outflow side 220b can be properly adjusted. The more the angle θ1 is increased thus reducing the angle θ2, the more an increase amount of pressure of a liquid to be displaced from the tube pump 500 can be increased.

The angle θ1 indicates a range where the second roller unit 20 moves before the first roller unit 10 starts separation from the tube 220 after the second roller unit 20 starts to come into contact with the tube 220. The angle θ2 indicates a range where the first roller unit 10 moves before the first roller unit 10 starts separation from the tube 220 after the second roller unit 20 starts to come into contact with the tube 220. In the tube pump 500 of this embodiment, an arcuate inner peripheral surface of the tube case 210 is formed within a range of an angle (θ1+θ2) about the axis line X1.

In this embodiment, the angle (θ1+θ2) is set larger than 180 degrees, and the arcuate inner peripheral surface of the tube case 210 is formed in the range of the angle (θ1+θ2). With such a configuration, compared to the case where the angle (θ1+θ2) is set smaller than 180 degrees, the angle θ1 is increased and, at the same time, the angle θ2 is reduced and hence, an increase amount of pressure of a liquid to be displaced from the tube pump 500 can be increased.

In the description made heretofore, the angle (θ1+θ2) is set larger than 180 degrees. However, it is more preferable that the angle (θ1+θ2) be increased as much as possible within a range smaller than an angle at which the first roller unit 10 and the second roller unit 20 are in contact with the tube 220 (for example, the angle (θ1+θ2) is smaller than 300 degrees).

Next, the attachment mechanism 300 in this embodiment is described with reference to FIG. 11 to FIG. 13.

Figure 11:
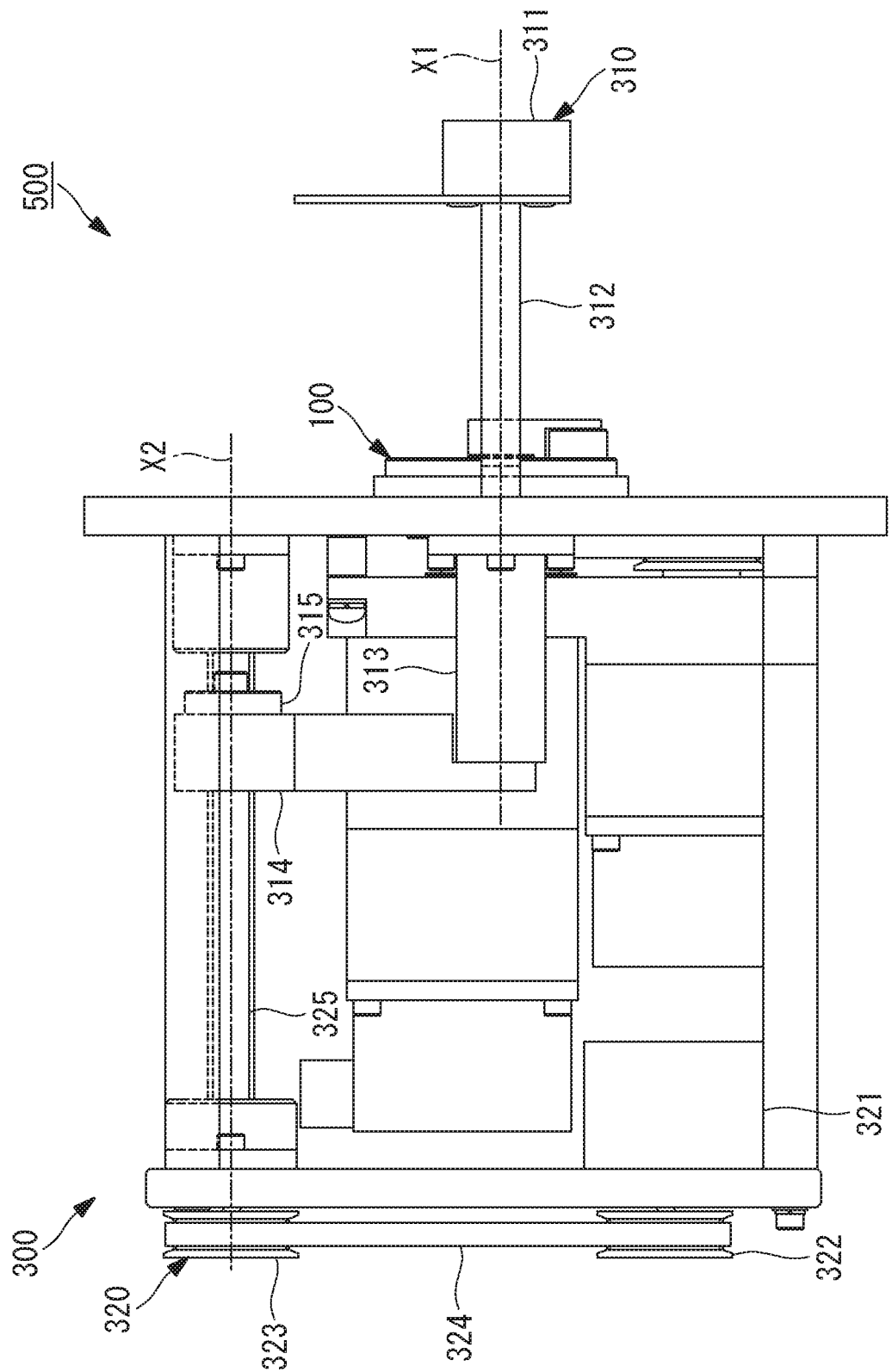
FIG. 11 is a front view of the tube pump shown in FIG. 1, and is also a view showing a state where the holding mechanism is not mounted on the attachment mechanism.

FIG. 11 is a front view of the tube pump 500 shown in FIG. 1, and is also a view showing a state where the holding mechanism 200 is not mounted on the attachment mechanism 300. FIG. 12 is a front view of the tube pump 500 shown in FIG. 1, and is also a view showing a state where the holding mechanism 200 is mounted on the attachment mechanism 300. FIG. 13 is a plan view of the housing mechanism 310 of the attachment mechanism 300 shown in FIG. 11 as viewed from above the tube pump 500.

Figure 12:
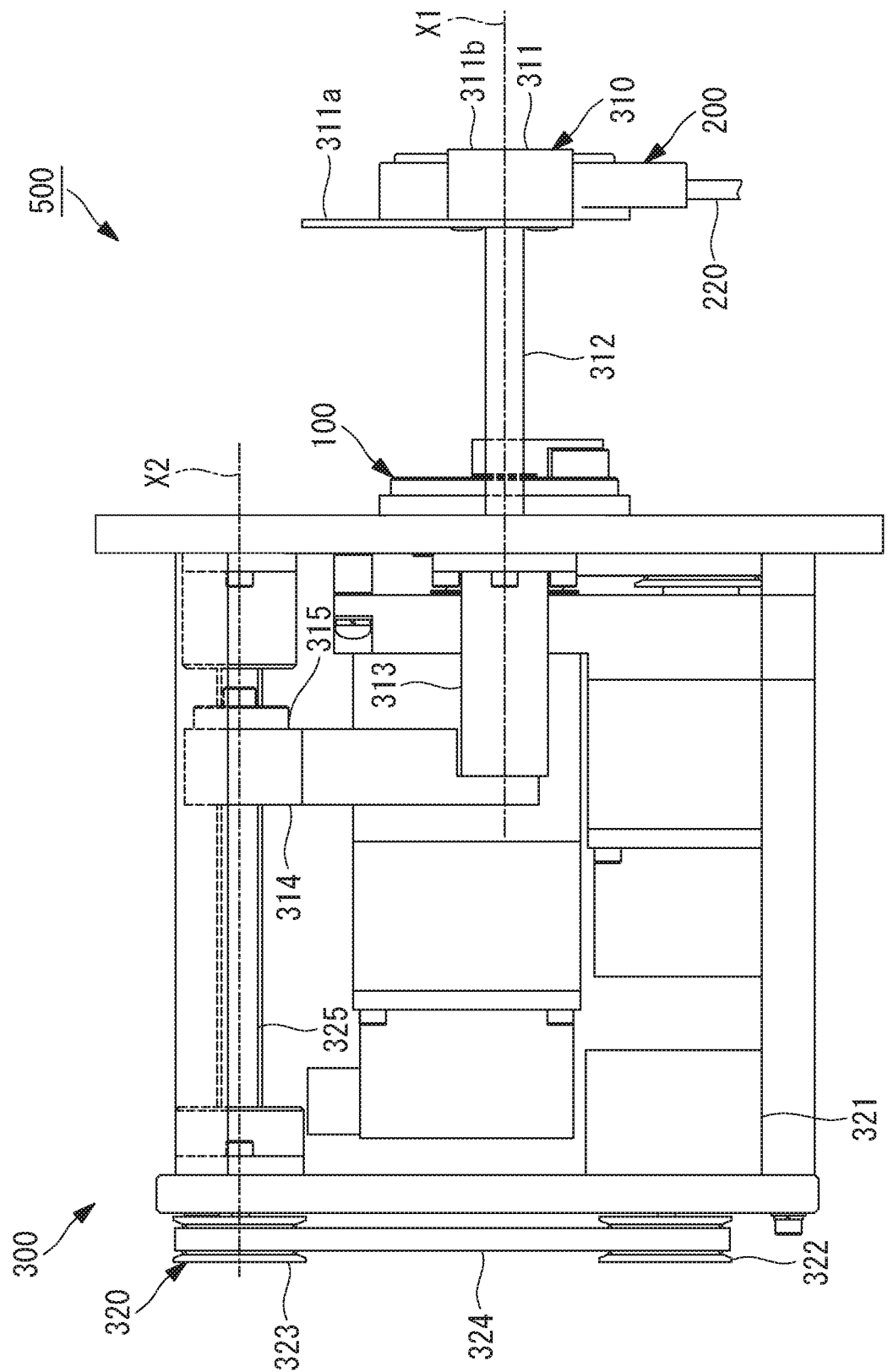
FIG. 12 is a front view of the tube pump shown in FIG. 1, and is also a view showing a state where the holding mechanism is mounted on the attachment mechanism.

As shown in FIG. 11 and FIG. 12, the attachment mechanism 300 includes: a housing mechanism 310 for housing and fixing the holding mechanism 200; and an advancing and retracting mechanism 320 for advancing and retracting the housing mechanism 310 along the axis line X1.

The housing mechanism 310 includes: a housing case 311 for housing the holding mechanism 200; a pair of first support shafts 312 for supporting the housing case 311; a pair of second support shafts 313 for supporting the pair of first support shafts 312; a holding member 314 for holding the pair of second support shafts 313; and a female threaded portion 315 attached to the holding member 314.

The advancing and retracting mechanism 320 includes: a drive motor 321; a drive pulley 322 driven by the drive motor 321; a driven pulley 323; a drive belt 324 for transmitting a drive force of the drive pulley 322 to the driven pulley 323; and a rotary shaft 325 which rotates about an axis line X2 together with the driven pulley 323.

The advancing and retracting mechanism 320 in this embodiment is a mechanism which can change over a state of the tube pump between a mounting state shown in FIG. 1 where the tube 220, the first roller unit 10, and the second roller unit 20 are disposed at the same position on the axis line X1 and a separated state shown in FIG. 12 where the holding mechanism 200 is disposed at the position separated from the drive mechanism 100 by a distance.

The drive motor 321 of the advancing and retracting mechanism 320 rotates in response to a control signal from the control unit 400 thus rotating the drive pulley 322. A drive force of the drive pulley 322 is transmitted to the driven pulley 323 through the drive belt 324 thus rotating the driven pulley 323 about the axis line X2. The rotary shaft 325 rotates about the axis line X2 together with the driven pulley 323.

A male thread is formed on an outer peripheral surface of the rotary shaft 325, and is fastened to the female threaded portion 315 of the housing mechanism 310. Accordingly, when the rotary shaft 325 rotates about the axis line X2, the female threaded portion 315 of the housing mechanism 310 moves along the axis line X2. The female threaded portion 315 is connected with the holding member 314, the pair of second support shafts 313, the pair of first support shafts 312, and the housing case 311. Therefore, when the female threaded portion 315 moves along the axis line X2, the entire housing mechanism 310 including the housing case 311 moves along the axis line X2.

In newly mounting the holding mechanism 200 on the tube pump 500, the control unit 400 drives the drive motor 321 of the advancing and retracting mechanism 320 thus bringing the tube pump 500 into the separated state shown in FIG. 11. Thereafter, an operator moves the holding mechanism 200 to the housing case 311 of the housing mechanism 310 while gripping the holding mechanism 200 so that the holding mechanism 200 is mounted on the tube pump 500.

Figure 13:
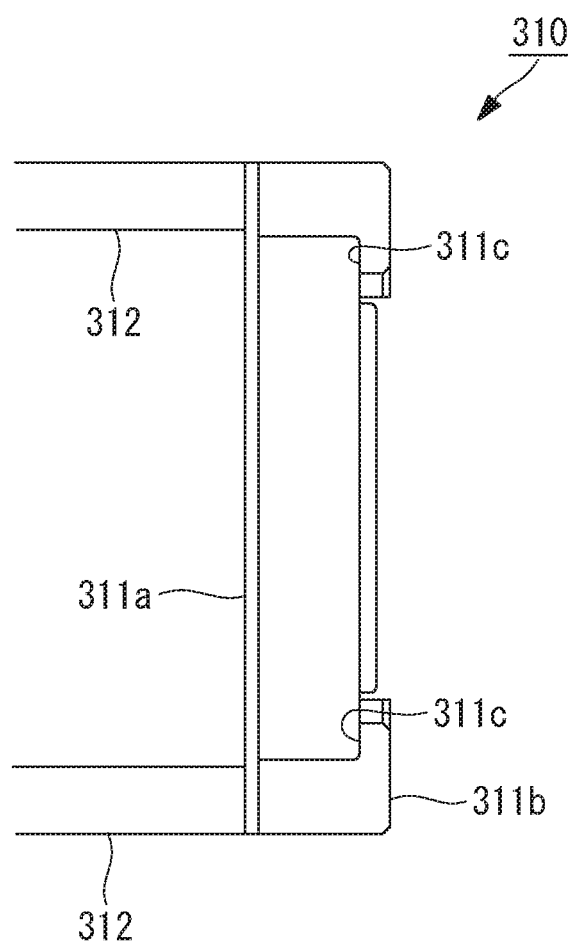
FIG. 13 is a plan view of a housing mechanism shown in FIG. 11 as viewed from above.

As shown in FIG. 12 and FIG. 13, the housing case 311 includes a set plate 311a formed into a plate shape and a case body 311b. A pair of housing grooves 311c for housing the pair of projections 212 of the holding mechanism 200 are formed on the case body 311b. The operator presses the back side of the holding mechanism 200 gripped by a hand of the operator to the set plate 311a and, thereafter, the pair of projections 212 of the holding mechanism 200 is housed in the pair of housing grooves 311c. With such operations, the operator can easily attach the holding mechanism 200 to the housing mechanism 310.

The holding mechanism 200 is attached to the housing mechanism 310 as shown in FIG. 12. Thereafter, the control unit 400 drives the drive motor 321 so as to move the housing mechanism 310 in the direction where the housing mechanism 310 approaches the drive mechanism 100 along the axis line X1. Therefore, the tube pump 500 is brought into a mounting state shown in FIG. 1 where the tube 220, the first roller unit 10, and the second roller unit 20 are disposed at the same position on the axis line X1.

The description is made with respect to the manner of operation of the drive mechanism 100 when the holding mechanism 200 is attached to the drive mechanism 100 by the attachment mechanism 300.

In response to a control signal from the control unit 400, the drive mechanism 100 in this embodiment can perform a displacement control mode (first control mode) where the first roller unit 10 and the second roller unit 20 are rotated in the same direction so as to displace a liquid in the tube 220 using the first roller unit 10 and the second roller unit 20.

In the displacement control mode, as shown in FIG. 9 and FIG. 10, at least either one of the first roller unit 10 or the second roller unit 20 is in contact with the tube 220 and hence, the replacement of the holding mechanism 200 cannot be performed. Further, when the first roller unit 10 and the second roller unit 20 are disposed at the position shown in FIG. 9 and FIG. 10 in a state where the holding mechanism 200 is not mounted on the drive mechanism 100, the tube 220 cannot be inserted into a gap formed between the respective roller units and the inner peripheral surface 211 of the tube case 210.

Accordingly, the drive mechanism 100 in this embodiment can perform a tube replacement mode (second control mode) in place of the displacement control mode in response to a control signal from the control unit 400.

In performing the tube replacement mode where the above-described mounting state and separated state are changed over, the control unit 400 fixes respective rotation angles of the first roller unit 10 and the second roller unit 20 so as to prevent the first roller unit 10 and the second roller unit 20 from coming into contact with the tube 220. The rotation angles at which the first roller unit 10 and the second roller unit 20 do not come into contact with the tube 220 are rotation angles shown in FIG. 14.

Figure 14:
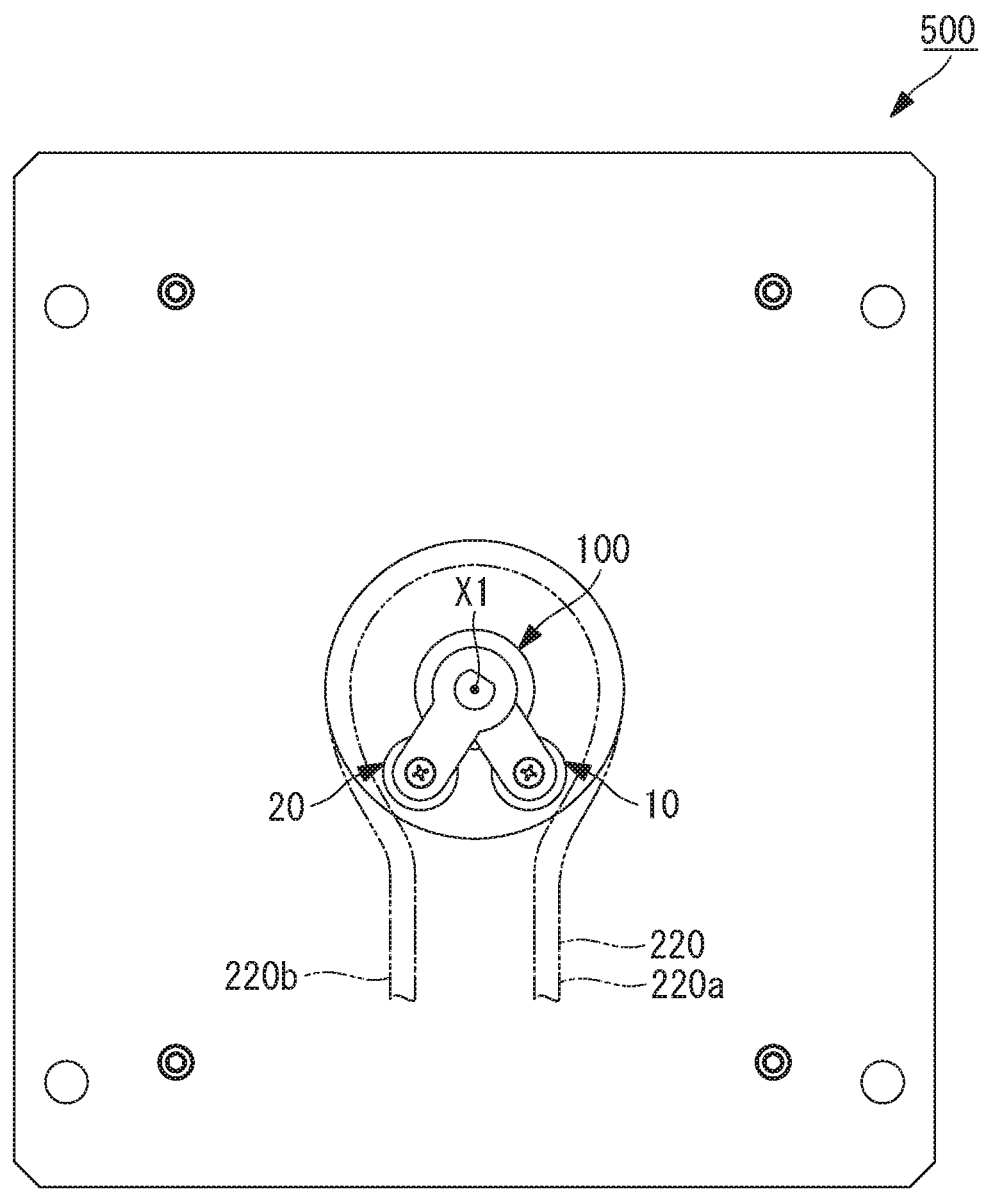
FIG. 14 is a partially enlarged view of the drive mechanism shown in FIG. 12.

FIG. 14 is a partially enlarged view of the drive mechanism 100 shown in FIG. 12. In FIG. 14, the position where the tube 220 is disposed when the holding mechanism 200 is mounted on the drive mechanism 100 is indicated by an imaginary line. As shown in FIG. 14, when the control unit 400 performs the tube replacement mode, the first roller unit 10 and the second roller unit 20 retract so as to prevent a contact with the tube 220.

Upon receipt of an instruction to change over between the above-described mounting state and separated state from an operator, the control unit 400 in this embodiment controls the advancing and retracting mechanism 320 and, at the same time, performs the tube replacement mode when a state of the tube pump is changed over from the separated state to the mounting state. Accordingly, in attaching the holding mechanism 200 to the drive mechanism 100 using the attachment mechanism 300, it is possible to prevent a problem where the tube 220 comes into contact with the first roller unit 10 and the second roller unit 20.

In the description made heretofore, the drive mechanism 100 can perform the displacement control mode and the tube replacement mode in response to a control signal from the control unit 400. However, the drive mechanism 100 may adopt another mode. For example, it may be configured such that the control unit 400 is incorporated into the drive mechanism 100, and the drive mechanism 100 controls the rotation of the first roller unit 10 performed by the first drive unit 50 and the rotation of the second roller unit 20 performed by the second drive unit 60.

The description is made with respect to the manner of operation and advantageous effects which the above-described tube pump 500 of this embodiment can acquire.

According to the tube pump 500 of this embodiment, the drive mechanism 100 includes the first roller unit 10, the second roller unit 20, the first drive unit 50, and the second drive unit 60. Accordingly, the first roller unit 10 and the second roller unit 20, which rotate while being in contact with the tube 220 held by the holding mechanism 200 in an arcuate shape about the axis line X1, can be independently rotated about the axis line X1.

According to the tube pump 500 of this embodiment, the holding mechanism 200 is detachably attached to the drive mechanism 100 by the attachment mechanism 300 so that the tube 220 can be easily replaced.

The tube pump 500 of this embodiment includes the control unit 400 for controlling the first drive unit 50 and the second drive unit 60. The control unit 400 can perform the displacement control mode (first control mode) where the first roller unit 10 and the second roller unit 20 are rotated in the same direction so as to convey a liquid in the tube 220, and the tube replacement mode (second control mode) where positions of the first roller unit 10 and the second roller unit 20 disposed about the axis line X1 are respectively fixed so as to prevent the first roller unit 10 and the second roller unit 20 from coming into contact with the tube 220.

According to the tube pump 500 of this embodiment, by performing the tube replacement mode, the first roller unit 10 and the second roller unit 20 can be fixed so as to prevent a contact with the tube 220. Accordingly, in attaching the holding mechanism 200 to the drive mechanism 100 using the attachment mechanism 300, the holding mechanism 200 can be easily and reliably attached to the drive mechanism 100 while preventing the tube 220 from coming into contact with the first roller unit 10 and the second roller unit 20. Further, by performing the displacement control mode after the holding mechanism 200 is attached to the drive mechanism 100 by the attachment mechanism 300, a liquid in the tube 220 can be conveyed.

In the tube pump 500 of this embodiment, the attachment mechanism 300 includes: the housing mechanism 310 for housing the holding mechanism 200; and the advancing and retracting mechanism 320 for advancing and retracting the housing mechanism 310 along the axis line X1. The advancing and retracting mechanism 320 is a mechanism capable of changing over a state of the tube pump between the mounting state where the tube 220, the first roller unit 10, and the second roller unit 20 are disposed at the same position on the axis line X1 and the separated state where the holding mechanism 200 is disposed at the position separated from the drive mechanism 100 by a distance.

According to the tube pump 500 of this embodiment, the holding mechanism 200 which is housed in the housing mechanism 310 is made to advance and retract along the axis line X1 by the advancing and retracting mechanism 320. With such a configuration, a state of the tube pump can be changed over reliably between the separated state and the mounting state while preventing the tube 220 from coming into contact with the roller unit.

In the tube pump 500 of this embodiment, the control unit 400 controls the advancing and retracting mechanism 320 so as to change over a state of the tube pump between the mounting state and the separated state, and the control unit 400 performs the tube replacement mode in changing over the state of the tube pump from the separated state to the mounting state.

With such a configuration, in attaching the holding mechanism 200 to the drive mechanism 100, the tube replacement mode is performed by the control unit 400 so that the roller units are fixed at the position where the roller units do not come into contact with the tube 220. Thereafter, the state of the tube pump is changed over from the separated state to the mounting state. Accordingly, in attaching the holding mechanism 200 to the drive mechanism 100, an operator is required to perform only a relatively simple operation, that is, to house the holding mechanism 200 in the housing mechanism 310.

The holding mechanism 200 of this embodiment is detachably attached to the drive mechanism 100 including the first roller unit 10 and the second roller unit 20 which rotate about the axis line X1 while being in contact with the tube 220 having elasticity. Further, the holding mechanism 200 includes: the tube case 210 on which the inner peripheral surface 211 is formed, the tube case 210 holding the tube 220 in an arcuate shape about the axis line X1; and the pair of fixing holes 213 for housing and fixing the pair of tube pressing rings 230 attached to the outer peripheral surface of the tube 220. The inner peripheral surface 211 is formed in a range larger than 180 degrees about the axis line X1.

According to the holding mechanism 200 of this embodiment, the inner peripheral surface 211 of the holding mechanism 200 is formed in a range larger than 180 degrees about the axis line X1. Accordingly, when the tube 220 is disposed along the inner peripheral surface 211 of the tube case 210, the tube 220 comes into contact with the arcuate inner peripheral surface 211 of the tube case 210 with a distance longer than a half of a circumference of an arcuate shape of the inner peripheral surface 211. With such a configuration, when the roller units rotate about the axis line X1, a range where the roller units come into contact with the tube 220 increases. Therefore, along with the increase in such a range, an amount of a liquid which is sandwiched between the pair of roller units increases. The larger an amount of the liquid becomes, the more an increase amount of pressure of a liquid which can be increased by the tube pump 500 increases so that pulsing of a liquid can be properly controlled.

In the holding mechanism 200 according to this embodiment, the tube case 210 is formed into a cylindrical shape, and one end of the tube case 210 in the direction of the axis line X1 is closed and the other end of the tube case 210 in the direction of the axis line X1 is opened. One end of the tube case 210 is closed so that a problem such as damage of the tube 220 carelessly caused by an operator can be suppressed. At the same time, the other end of the tube case 210 is opened so that the holding mechanism 200 can be attached to the drive mechanism 100.

Other Embodiment

In the description made heretofore, the attachment mechanism 300 is configured to move the housing mechanism 310 along the axis line X1 by a drive force of the drive motor 321. However, the attachment mechanism 300 may adopt another mode. For example, instead of using a drive force of the drive motor 321, an operator may operate the advancing and retracting mechanism 320 so as to apply power to the advancing and retracting mechanism 320.

Further, for example, the advancing and retracting mechanism 320 may not be provided, and the holding mechanism 200 may be directly attached to the drive mechanism 100 using fastenings. Also in the above-mentioned case, the control unit 400 performs the tube replacement mode so that it is possible to prevent a problem where the tube 220 comes into contact with the first roller unit 10 and the second roller unit 20 when the holding mechanism 200 is attached to the drive mechanism 100.

The invention claimed is:

1. A tube pump comprising:
a drive mechanism including a pair of contact members configured to rotate about an axis line while being in contact with a tube having elasticity, and a pair of drive units configured to cause the pair of contact members to rotate independently about the axis line;
a holding mechanism configured to hold the tube in an arcuate shape about the axis line;
an attachment mechanism configured to detachably attach the holding mechanism to the drive mechanism, and
a control unit configured to control the pair of drive units, wherein the control unit is capable of performing a first control mode where the pair of contact members are rotated in the same direction so as to convey a liquid in the tube, and a second control mode where positions of the pair of contact members disposed about the axis line are respectively fixed so as to prevent the pair of contact members from coming into contact with the tube.

2. The tube pump according to claim 1, wherein the attachment mechanism includes:
a housing mechanism configured to house and fix the holding mechanism; and
an advancing and retracting mechanism configured to advance and retract the housing mechanism along the axis line,
wherein the advancing and retracting mechanism is a mechanism capable of changing over a state of the tube pump between a mounting state where the tube and the pair of contact members are disposed at the same position on the axis line and a separated state where the holding mechanism is disposed at a position separated from the drive mechanism by a distance.

3. The tube pump according to claim 1,
the holding mechanism further comprising:
a holding portion on which an inner peripheral surface is formed, the holding portion holding the tube in an arcuate shape about the axis line; and
a pair of fixing portions configured to house and fix a pair of positioning members attached to an outer peripheral surface of the tube, wherein the inner peripheral surface is formed in a range larger than 180 degrees about the axis line.

4. The tube pump according to claim 3, wherein the holding portion is formed into a cylindrical shape, and one end of the holding portion in a direction of the axis line is closed and the other end of the holding portion in the direction of the axis line is opened.

5. A tube pump comprising:
a drive mechanism including a pair of contact members configured to rotate about an axis line while being in contact with a tube having elasticity, and a pair of drive units configured to cause the pair of contact members to rotate independently about the axis line;
a holding mechanism configured to hold the tube in an arcuate shape about the axis line;
an attachment mechanism configured to detachably attach the holding mechanism to the drive mechanism, and
a control unit configured to control the pair of drive units, wherein the control unit is capable of performing a first control mode where the pair of contact members are rotated in the same direction so as to convey a liquid in the tube, and a second control mode where positions of the pair of contact members disposed about the axis line are respectively fixed so as to prevent the pair of contact members from coming into contact with the tube,
wherein the attachment mechanism includes:
a housing mechanism configured to house and fix the holding mechanism; and
an advancing and retracting mechanism configured to advance and retract the housing mechanism along the axis line, wherein the advancing and retracting mechanism is a mechanism capable of changing over a state of the tube pump between a mounting state where the tube and the pair of contact members are disposed at the same position on the axis line and a separated state where the holding mechanism is disposed at a position separated from the drive mechanism by a distance,
wherein the control unit is configured to control the advancing and retracting mechanism so as to change over a state of the tube pump between the mounting state and the separated state, and the control unit is configured to perform the second control mode in changing over the state of the tube pump from the separated state to the mounting state.

* * * * *